(12) United States Patent
Medoff

(10) Patent No.: US 11,559,299 B2
(45) Date of Patent: Jan. 24, 2023

(54) METHOD AND APPARATUS FOR DIRECTING AN ELONGATE FLEXIBLE COMPONENT THROUGH A PART OF A HUMAN BODY

(71) Applicant: TriMed, Incorporated, Santa Clarita, CA (US)

(72) Inventor: Robert Medoff, Kailua, HI (US)

(73) Assignee: Trimed, Incorporated, Santa Clarita, CA (US)

( * ) Notice: Subject to any disclaimer, the term of this patent is extended or adjusted under 35 U.S.C. 154(b) by 0 days.

(21) Appl. No.: 17/130,809

(22) Filed: Dec. 22, 2020

(65) Prior Publication Data

US 2021/0196260 A1    Jul. 1, 2021

Related U.S. Application Data

(60) Provisional application No. 62/953,749, filed on Dec. 26, 2019.

(51) Int. Cl.
| | | |
|---|---|---|
| *A61B 17/04* | (2006.01) | |
| *A61B 17/84* | (2006.01) | |
| *A61B 17/16* | (2006.01) | |
| *A61B 17/88* | (2006.01) | |
| *A61B 17/56* | (2006.01) | |

(52) U.S. Cl.
CPC ...... *A61B 17/0482* (2013.01); *A61B 17/1697* (2013.01); *A61B 17/842* (2013.01); *A61B 17/8861* (2013.01); *A61B 2017/564* (2013.01)

(58) Field of Classification Search
CPC .... A61B 17/06004; A61B 2017/06014; A61B 2017/06019; A61B 2017/06066; A61B 17/083; A61B 2017/086; A61B 2017/088; A61F 2/08–0811; A61F 2002/085–0894
See application file for complete search history.

(56) References Cited

U.S. PATENT DOCUMENTS

| | | | | |
|---|---|---|---|---|
| 4,583,540 A | * | 4/1986 | Malmin | ..................... A61F 2/10 606/103 |
| 4,957,502 A | * | 9/1990 | Takase | ............. A61B 17/06066 606/223 |
| 5,055,105 A | | 10/1991 | Hamlin et al. | |

(Continued)

OTHER PUBLICATIONS

International Search Report and Written Opinion, dated Mar. 18, 2021 in International Application No. PCT/US20/66643.

*Primary Examiner* — Matthew J Lawson
(74) *Attorney, Agent, or Firm* — Wood, Phillips, Katz, Clark & Mortimer

(57) ABSTRACT

A method of, and apparatus for, directing an elongate flexible component with a length through a part of a human body. The method includes the steps of: obtaining an apparatus having an elongate body with a length between axially spaced leading and trailing ends and a notch through a peripheral surface of the elongate body; directing a mid-length part of the elongate flexible component into the notch to place the elongate flexible component into an operative position on the apparatus; and with the elongate flexible component in the operative position, advancing the elongate body through the part of the human body and thereby causing a portion of the elongate flexible component to be drawn by a drawing surface on the elongate body through the part of the human body.

30 Claims, 3 Drawing Sheets

(56) References Cited

U.S. PATENT DOCUMENTS

| | | | | |
|---|---|---|---|---|
| 5,747,770 | A * | 5/1998 | Bogart | B23K 26/389 |
| | | | | 219/121.72 |
| 6,056,771 | A * | 5/2000 | Proto | A61B 17/2909 |
| | | | | 606/224 |
| 6,322,581 | B1 | 11/2001 | Fukuda et al. | |
| 2010/0217315 | A1 * | 8/2010 | Jolly | A61B 17/06 |
| | | | | 606/223 |
| 2012/0083837 | A1 * | 4/2012 | Ferragamo | A61B 17/06004 |
| | | | | 606/232 |
| 2014/0257377 | A1 * | 9/2014 | Akutsu | A61B 17/06004 |
| | | | | 606/223 |
| 2016/0361090 | A1 | 12/2016 | Taylor | |
| 2018/0199936 | A1 * | 7/2018 | Kelner | A61B 17/06166 |
| 2018/0206838 | A1 * | 7/2018 | Miraki | A61B 17/06004 |
| 2019/0015098 | A1 | 1/2019 | Schamblin | |
| 2020/0155137 | A1 * | 5/2020 | Brunsvold | A61B 17/0401 |

\* cited by examiner

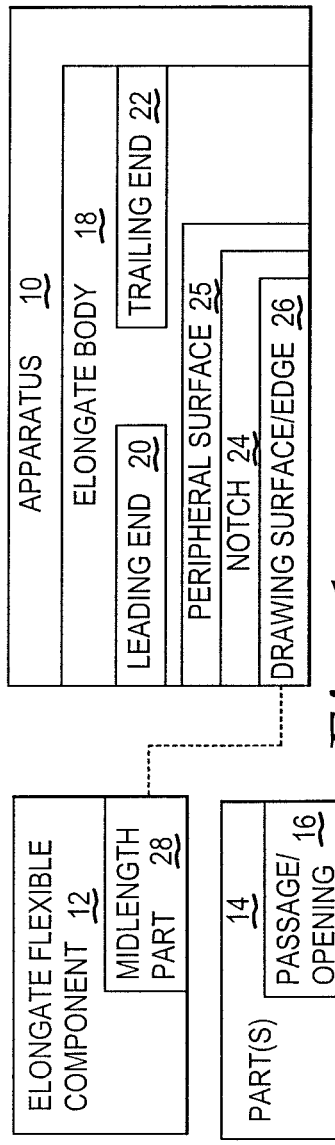
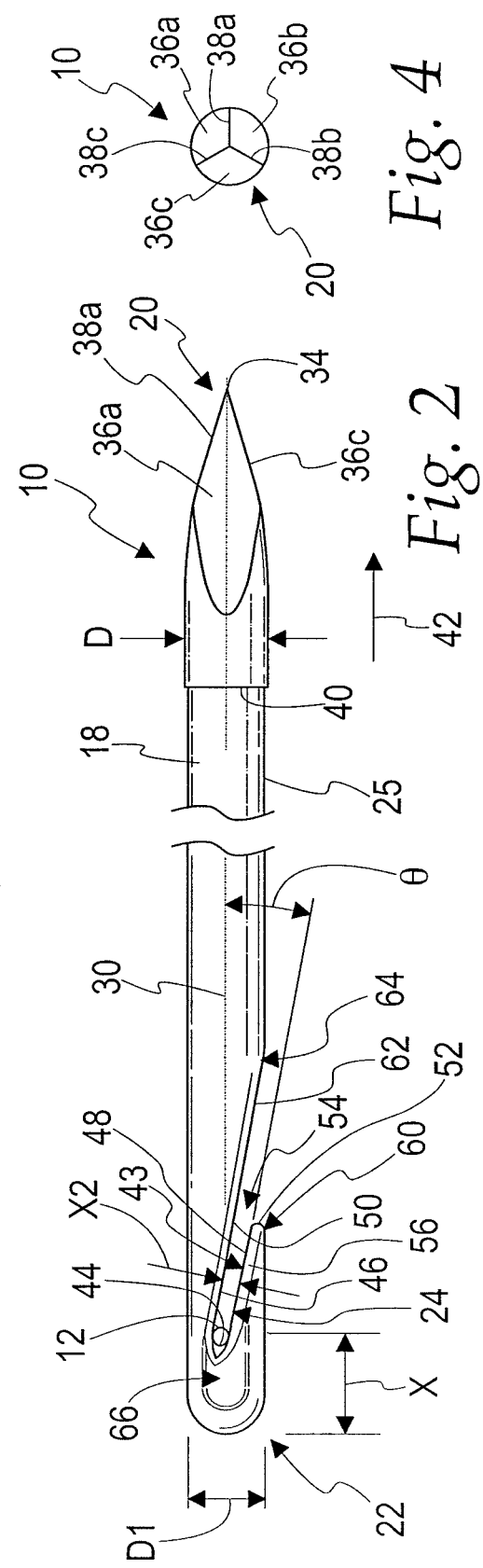

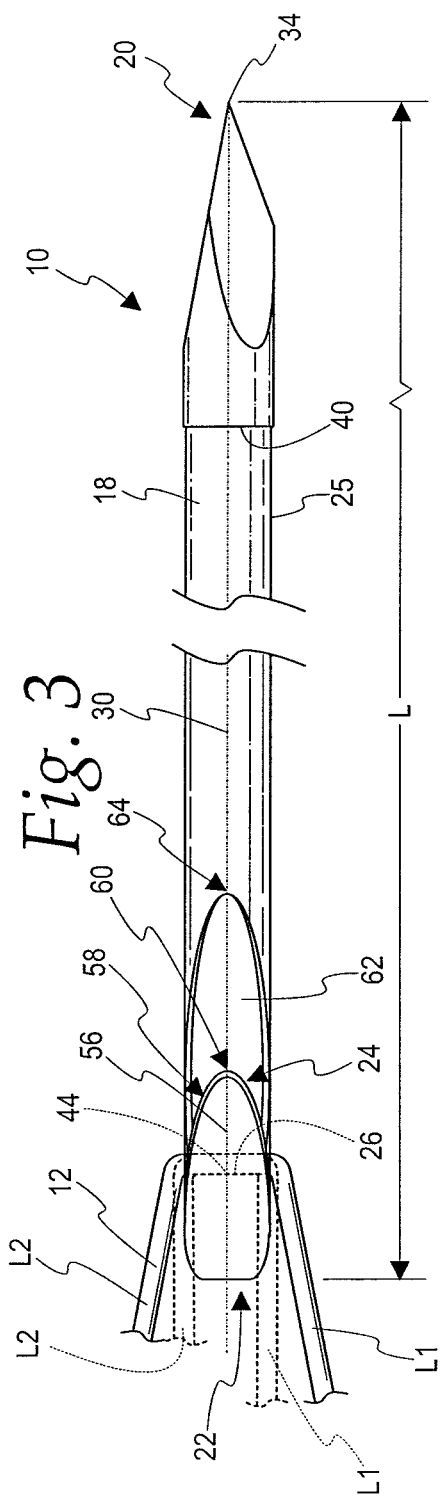
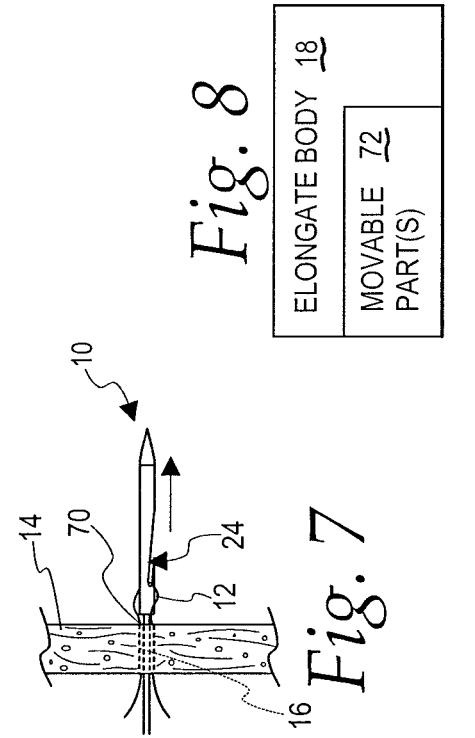
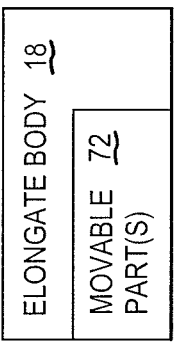
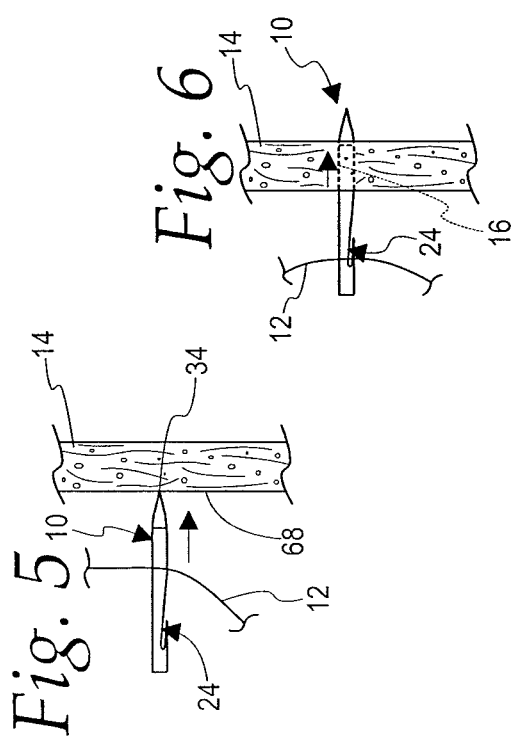

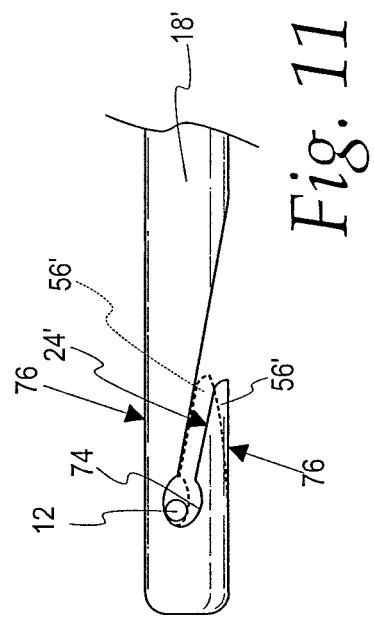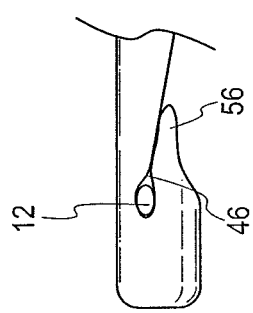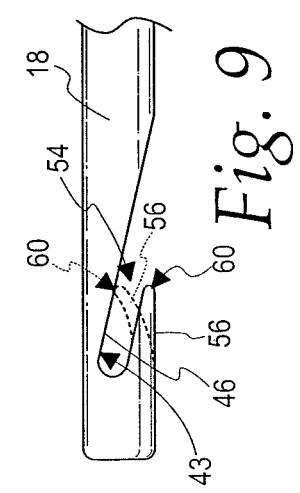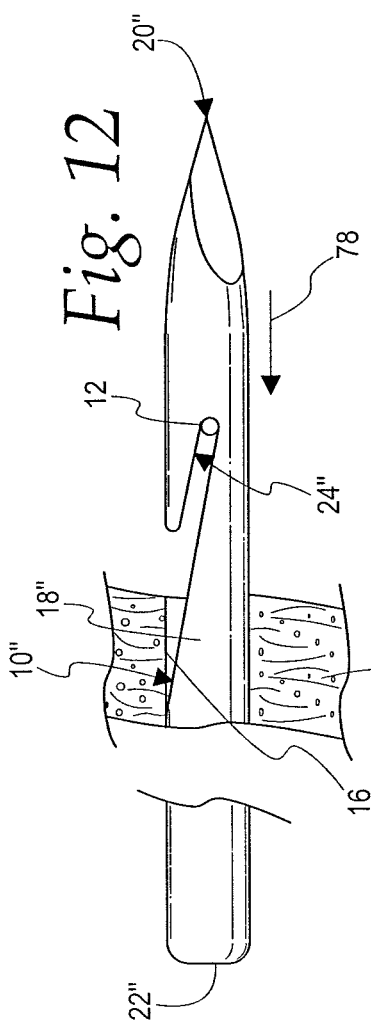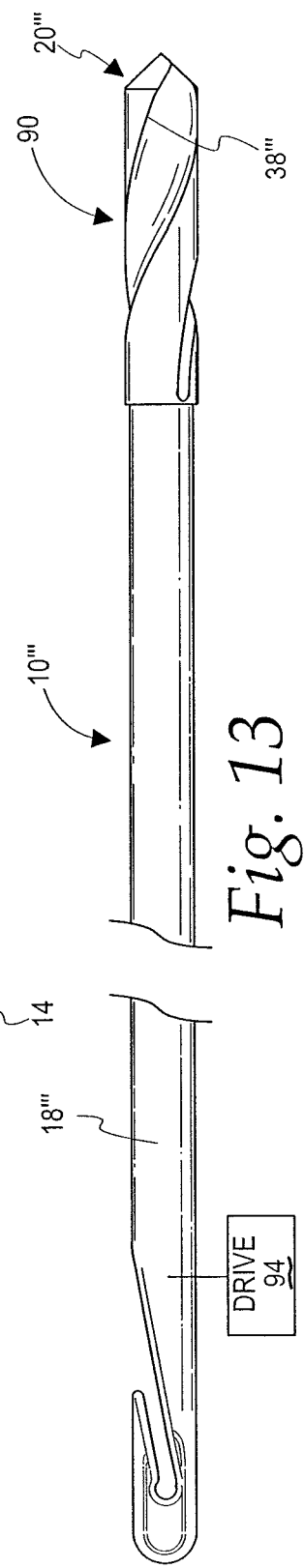

METHOD AND APPARATUS FOR DIRECTING AN ELONGATE FLEXIBLE COMPONENT THROUGH A PART OF A HUMAN BODY

BACKGROUND OF THE INVENTION

Field of the Invention

This invention relates to medical procedures and, more particularly, to a method and apparatus for directing an elongate flexible component, such as a suture, through part of a patient's body made up of soft tissue and/or bone.

Background Art

In many medical procedures, a surgeon is required to direct an elongate flexible component through different parts of a patient's body made up of soft tissue and/or bone. While the invention herein is not limited to a particular form of flexible component, for purposes of simplicity, a suture will be used as an exemplary form throughout. In performing the procedure, the suture will be passed through one or more soft tissues and/or one or more bones/bone parts. Again, for purposes of simplicity, and without limiting the scope of the invention herein, the focus will be principally upon directing a suture through bone, which is generally more difficult due to the hardness thereof.

Currently, there are a number of different ways to direct a suture through bone. In one form, a passage/channel for a rigid needle is pre-formed in the bone such as with a drill or pin. The needle typically has a relatively rigid metal construction with either a curved or straight shape. There are a number of needle configurations currently being utilized. Commonly, a free suture end is threaded through a fully surrounded needle opening and doubled back on itself. The needle draws the thread with it as the needle is advanced through a bone passage. Alternatively, the suture may be integrally connected to the needle, such as by providing a small cannulated channel at the end of the needle, inserting the suture end therein, and crimping the surrounding needle portion against the suture thread.

With the through passage formed, an entry to the passage is located and the leading end of the needle introduced with the operatively positioned suture. In the event that the passage traverses more than one bone and/or bone part, it may be particularly difficult or even impossible to find the entry location in the second bone/bone part, especially if the second bone has moved in position after the passage is drilled. Aside from adding time to the overall procedure, any delay in effecting introduction of the needle may create frustration that causes fatigue in an already stressful endeavor. The inability to find the passage can also compromise the effectiveness of the procedure. Further, needles typically come in a limited number of different lengths so that matching the needle to the task may be problematic, which may lead to a certain awkwardness or complication in a procedure.

Another technique involves the formation of a drawing loop. Commonly, a small suture will be used and doubled up as a loop or tied using a looped knot at one end. The surgeon is required to pass the suture through a formed passage, whereupon the loop can be connected to the active suture and used to pull that suture through the passage. With a large passage diameter, especially when the passage is through a single bone, this procedure may be practical, assuming the overall passage length is relatively short. However, if the effective diameter of the passage is small and/or the distance the suture must pass through is large, or through multiple bones, the process may be very difficult or impossible to perform. Sutures generally are difficult to thread by reason of their flexibility and tendency to snag and bend as they are directed through a surrounded passage/bore. Once again, delays in a procedure are detrimental in terms of efficiency and contributing to surgeon fatigue, which could result in an inability of a surgeon to complete a procedure.

A further technique uses an instrument to reposition the suture itself. One example practiced uses what is known as a Hughston suture passer. This apparatus is in the form of a long, thin, pin, commonly with a small handle, that has a closed loop of flexible line attached at its end. The loop is directed by the surgeon through a pre-formed passage. Once the loop exits the passage, a suture can be passed through the closed loop, whereupon the loop can be withdrawn. Generally, this, and the previously described conventional techniques, require use of multiple pieces, assembly, and confirmation of interface strength. Each of the above techniques requires introduction of a free end of a suture, whether single or looped back on itself, controllably into a closed loop or needle "eye" to perform the necessary steps. In addition, this approach requires that the passage is first formed by drilling, after which the instrument is passed through the pre-formed passage. This requires that the passage be larger than the instrument to allow easy passage therethrough. Additionally, and particularly when the passage is through multiple bones, movement of one bone relative to another can make traversing of the entire passage difficult or even impossible.

A further known technique involves directing a suture through an eyelet at the end of a pin, which is used effectively like a needle. However, this technique employs a pin with a tip that has a cutting edge. The pin that carries the suture is the same structure that is used to bore the bone to create the passage through the bone and draw the suture through the formed bone passage. This simplifies the process compared to the prior art discussed above in that the surgeon is not required to have on hand and utilize a separate boring instrument and suture drawing structure and eliminates the need to find a previously formed passage. Thus, the number of pieces required to be kept on hand during this type of procedure is reduced, as is the time required by reason of performing two steps as one. However, since the suture is attached to the pin, when the apparatus is rotated through the drilling operation to produce the passage, the suture follows the rotation and spins/wraps behind the pin. The resulting structure may have the appearance of a tangled fishing line, which creates other complications, including the inconvenience of having to untangle the line adequately to allow it to be manipulated and tied to achieve the desired end result. In addition, given the flexible nature of the suture, and other flexible components, together with the tendency of the suture ends to fray, the "threading" process may be difficult or impractical, particularly as a step required to be performed during a surgical procedure.

In spite of the frequency that procedures are performed with suture manipulation as described above, through both hard and soft tissues, no existing structure known to the inventor herein effectively addresses at least those issues identified above. In surgical procedures, efficiency and ease of performance are critical guides to design. It is believed that the prior art has not adequately achieved these design objectives.

SUMMARY OF THE INVENTION

In one form, the invention is directed to a method of directing an elongate flexible component with a length through a part of a human body. The method includes the steps of: obtaining an apparatus having an elongate body with a length between a leading end and a trailing end, the elongate body having a lengthwise axis and a peripheral surface extending around the axis, the body further having a notch through the peripheral surface and a drawing surface; directing a midlength part of the elongate flexible component into the notch to thereby place the elongate flexible component in an operative position on the apparatus; and with the elongate flexible component in the operative position, advancing the elongate body through the part of the human body in a first direction and thereby causing a portion of the elongate flexible component to be drawn by the drawing surface through the part of the human body.

In one form, the step of advancing the elongate body involves advancing the elongate body so that the notch moves fully through the part of the human body.

In one form, the step of advancing the elongate body involves advancing the elongate body fully through part of the human body.

In one form, the elongate body has a cutting edge at the leading end of the elongate body. The method further includes the step of using the cutting edge to create or enlarge a passage within the part of the human body through which the elongate flexible component is directed.

In one form, the step of directing the midlength part of the elongate flexible component into the notch involves sliding the midlength part of the elongate flexible component against and axially along the peripheral surface of the elongate body up to and into the notch.

In one form, the step of directing the midlength part of the elongate flexible component into the notch involves slidably guiding the midlength part of the elongate flexible component inwardly from the outside surface along a guide surface portion at an acute angle to the lengthwise axis.

In one form, the step of directing the midlength part of the elongate flexible component into the notch involves guiding the midlength part of the elongate flexible component lengthwise along the elongate body up to and against the drawing edge.

In one form, the step of creating or enlarging a passage involves turning the leading end of the elongate body to cause the cutting edge to sever the part of the human body before directing the midlength part of the elongate flexible component into the notch.

In one form, the part of the human body is one of a bone/bone part and soft tissue.

In one form, the method further includes the step of directing the elongate body, leading end first, in a second direction opposite to the first direction, through the part of the human body to expose the notch before directing the midlength part of the elongate flexible component into the notch. The step of advancing the elongate body involves moving the elongate body with the elongate flexible component in the operative position, trailing end first, in the first direction to thereby separate the apparatus from the part of the human body.

In one form, the method further includes the step of reconfiguring the apparatus to assist maintaining the elongate flexible component in the operative position.

In one form, the step of reconfiguring the apparatus involves deforming a part of the apparatus.

In one form, the notch has an entry location through which the midlength part of the elongate flexible component is directed to place the elongate flexible component in the operative position. The step of reconfiguring the apparatus involves changing at least one of a shape and size of the entry location.

In one form, the elongate body has at least one deformable part. The step of reconfiguring the apparatus involves deforming the at least one deformable part to thereby cause a part of the elongate flexible element to be fixedly captured on the elongate body.

In one form, the part of the apparatus that is deformed is a cantilevered part bounding a part of the notch. The cantilevered part is integrally formed with the elongate body and bent to perform the step of reconfiguring the apparatus.

In one form, the step of reconfiguring the apparatus involves crimping a region of the apparatus.

In one form, the notch has a volume bounded by the drawing surface. The drawing surface is exposed within the notch volume.

In one form, the elongate flexible component is placed in the operative position after the leading end of the elongate body is directed into the part of the human body.

In one form, the method further includes the step of separating the elongate flexible component from the elongate body after the elongate body is advanced fully through the body part.

In one form, the elongate flexible component is a suture.

In one form, the step of advancing the elongate body through the part of the human body in the first direction involves advancing the elongate body leading end first.

In one form, the method further includes the step of pre-forming an opening through the part of the human body before introducing the elongate body into the opening through the part of the human body.

In one form, the elongate body has a stepped diameter with a larger diameter portion and a smaller diameter portion, with the larger diameter portion closer to the leading end of the elongate body than the smaller diameter portion.

In one form, the invention is directed to the combination of: an elongate flexible component with a length for direction through a part of a human body; and an apparatus having an elongate body with a length between a leading end and a trailing end. The body has an axis, a peripheral surface extending around the axis, a notch through the peripheral surface, and a drawing surface. The leading end of the elongate body is configured to be directed through a part of a human body. The notch is configured so that a midlength part of the elongate flexible component can be directed into the notch to bear against the drawing surface with the elongate flexible component in an operative position. A part of the elongate flexible component can be drawn by the drawing surface so as to thereby move with the elongate body as the elongate body is advanced into and through a part of a human body sufficiently to be engaged and separated from the apparatus.

In one form, the elongate flexible component is a suture.

In one form, the leading end of the elongate body has a sharp tip.

In one form, the leading end of the elongate body has a cutting edge extending lengthwise of the elongate body that is configured to form or enlarge a passage through a part of a human body as the edge is borne against a part of a human body and the elongate body is turned around the axis of the elongate body.

In one form, the leading end of the elongate body has a plurality of cutting edges each extending lengthwise of the elongate body and configured to form or enlarge a passage through a part of a human body as the edge is borne against a part of a human body and the elongate body is turned around the axis of the elongate body.

In one form, the elongate body has a length between 3 and 5 inches.

In one form, the elongate body is substantially cylindrical in shape with a diameter of 0.05 to 0.07 inches.

In one form, the notch is closer to the trailing end of the elongate body than to the leading end of the elongate body.

In one form, the notch is closer to the leading end of the elongate body than the trailing end of the elongate body.

In one form, the notch has a "U" shape as viewed from a radial perspective.

In one form, the "U" opens in a direction that is at an acute angle to the axis of the elongate body.

In one form, the notch has an entry location. The "U" shape is bounded by at least one cantilevered part that is bendable to change at least one of a size and shape of the entry location.

In one form, the cantilevered part has a rounded free end.

In one form, the notch on the elongate body is bounded by a surface including at least one portion extending at an acute angle to the axis of the elongate body.

In one form, the at least one surface portion resides in a plane that makes an angle of 5°-15° with the axis of the elongate body.

In one form, the elongate body is made from stainless steel.

In one form, the elongate body is locally radially enlarged adjacent to the leading end.

In one form, the at least one cantilevered part is bendable to substantially fully block the entry location.

In one form, the elongate body is deformable by bending the at least one cantilevered part to crimp a part of the elongate flexible component with the elongate flexible component in the operative position.

In one form, the elongate body has a discrete sub-receptacle which remains open to allow the elongate flexible component to be moved therethrough with the cantilevered part bent against another part of the elongate body.

BRIEF DESCRIPTION OF THE DRAWINGS

FIG. 1 is a schematic representation of an apparatus, according to the invention, for directing an elongate flexible component through a part of a human body, as also shown schematically in FIG. 1;

FIG. 2 is a side elevation view of one specific form of the apparatus as shown schematically in FIG. 1;

FIG. 3 is a view as in FIG. 2 with the apparatus turned through 90° around a lengthwise axis and with an elongate flexible component in an operative position thereon;

FIG. 4 is an end elevation view of the apparatus in FIGS. 2 and 3;

FIGS. 5-7 are schematic representations showing sequential steps performed using the inventive apparatus to direct an elongate, flexible component through a bone;

FIG. 8 is a schematic representation of the elongate body on the apparatus in FIG. 1 and having a reconfigurable form;

FIG. 9 is an enlarged, fragmentary, elevation view showing the apparatus in FIGS. 2-4 and reconfigured to more positively maintain the elongate flexible component in its operative position;

FIG. 10 is fragmentary view as in FIG. 9 with the elongate body reconfigured to crimp the elongate flexible component in its operative position;

FIG. 11 is a view as in FIG. 10 showing a modified form of the inventive apparatus;

FIG. 12 is a view corresponding to that in FIG. 2 and showing a further modified form of apparatus wherein an elongate flexible component is moved in an opposite direction through a bone; and FIG. 13 is a view as in FIG. 2 and showing a further modified form of apparatus with a different form of leading end.

DETAILED DESCRIPTION OF THE PREFERRED EMBODIMENT

As shown schematically in FIG. 1, the invention is directed to an apparatus 10 usable to direct an elongate flexible component 12 through at least one part 14 of a human body. The schematic showing in FIG. 1 is intended to encompass different forms of the apparatus 10 as well as different applications through use of different forms of the elongate flexible component 12 through one or more human body parts 14.

For example, the part(s) 14 may be any soft tissue and/or bone/bone part and different combinations thereof, including, for example, multiple bones/bone parts, etc. As noted above, the emphasis herein will be principally on the part 14 being in the form of a bone which requires more difficult passage formation by reason of the hardness of the bone. The invention contemplates that the apparatus 10 can be usable to form and/or enlarge a pre-formed passage/opening 16 through the part(s) 14.

Similarly, the elongate flexible component 12 may take a number of different forms, any of which requires advancement from an entry opening to the passage 16 to and through an exit opening to allow an appropriate procedure to be performed. Again, as noted above, for purposes of simplicity, the invention herein will be focused on the use of an elongate flexible component 12 in the form of a conventional suture that is drawn through the passage 16 defined through one or more parts 14 to allow manipulation of the suture, as to form a restrictive loop, or for any other purpose in the medical field.

The apparatus 10, in its most basic form, consists of an elongate body 18 with a lengthwise axis and axially spaced leading and trailing ends 20, 22, respectively. The elongate body 18 has a notch 24 formed through a peripheral surface 25 extending around the lengthwise axis. A drawing surface/edge 26 on the elongate body 18 is accessed through the notch 24. For simplicity, the drawing surface/edge 26 will be identified generally as a drawing "surface."

The apparatus 10, and particularly the notch 24 thereon, are configured so that a midlength part 28 of the elongate flexible component 12 can be directed into the notch 24 and against the drawing surface 26, which represents an operative position for the elongate flexible component, wherein the drawing surface 26 draws the elongate flexible component 12 therewith as the apparatus 10 is moved through the passage 16 on the part(s) 14 of the human body.

As used herein, "notch" includes any opening through the peripheral surface 25, regardless of how it is formed or its precise shape, that permits entry of the midlength part 28 and passage through a volume formed by the notch to abut to the drawing surface 25. The notch as viewed from a radial perspective may have an unlimited number of different shapes, among which, but not limiting, are generally U-shaped and V-shaped either symmetrical or non-symmetrical on sides of an axis, etc. The drawing surface 26 may reside within the notch volume or may be within a sub-volume in communication with the notch volume.

The apparatus 10 is shown in schematic form since the construction of each of the parts thereof, and their interaction, may vary over a wide range. The configuration of the apparatus 10 is preferably such that a surgeon does not have to thread the elongate flexible component 12, end first, into the notch 24 to place the elongate flexible component 12 in the operative position. Instead, the midlength part 28 can be readily moved directly into the notch 24 and to against the drawing surface 26 or guided into that operative position by the elongate body 18.

A specific form of the apparatus 10 will now be described, with it being understood that this particular form is exemplary in nature only. The generic showing of the apparatus 10 in FIG. 1 is intended to encompass the specific forms described below as well as virtually a limitless number of variations thereof which may involve reconfiguration of one or more of the parts thereof and/or their interaction.

Referring now to FIGS. 2-4, the elongate body 18 on the apparatus 10 has a substantially cylindrical configuration between its leading and trailing ends 20, 22, respectively. In this embodiment, the elongate body 18 is substantially straight between the ends 20, 22, though this is not required. The cylindrical shape has a central axis 30. The peripheral surface 25 of the elongate body 18 extends around the axis 30.

The leading end 20 has a sharp tip 34. Three circumferentially spaced regions 36a, 36b, 36c are formed at the leading end region and produce at their junctures sharp cutting edges 38a, 38b, 38c. The cutting edges 38 are substantially straight, extend lengthwise of the elongate body 18, and converge forwardly to the tip 34. The regions 36 may be appropriately contoured to produce the desired sharpened cutting edges 38 therebetween. As just one example, without limitation, the regions 36 may be substantially flat.

The elongate body 18 has a stepped diameter at the peripheral surface 25. The elongate body 18 is locally radially enlarged adjacent to the leading end 20 and has a diameter D that is slightly greater than the diameter D1, with the diameter D1 being substantially constant from a step 40, where the two different diameters meet, up to the trailing end 22 of the elongate body 18. This precise construction is not required, however.

With the depicted configuration, the tip 34 can be placed at the bone location where passage formation or enlargement is required. A forward pressure can be exerted on the elongate body 18 while the elongate body 18 is turned either continuously or back and forth around the axis 30 to cause the cutting edges 38 to progressively remove bone material, which is made possible by the tapered cutting edge region. The cutting edges 38 produce the passage diameter D which thereby provides clearance for the trailing smaller diameter portion of the elongate body 18 so that it does not bind detrimentally within the passage 16 as the elongate body 18 is advanced forwardly in the direction of the arrow 42.

An exemplary diameter D1 would be at least 0.004" smaller than the diameter D to allow the apparatus to be withdrawn without drilling once the tip 34 has cleared the bone. The precise dimensions for D1 and D2 are not critical. As just an example, the dimension D1 may be in a range of 0.05-0.07 inches. However, dimensions potentially significantly outside this range—either above or below—are contemplated.

Similarly, the overall length L of the elongate body 18 is dictated by the particular application. In one exemplary form, the length L is on the order of 3.937 inches, but may be in the range of 3-5 inches or, again, outside of this range—either above or below—depending upon the application.

Typically, the material making up the elongate body 18 will be metal, such as stainless steel or other medical grade elements and/or alloys.

The volume of the notch 24 is bounded by a surface 43, which in this case is shown as U-shaped, opening at an acute angle θ to the axis 30 in a leading direction, as viewed from the radial perspective of FIG. 2. In this exemplary form, the notch 24 is formed closer to the trailing end 22 than the leading end 20 but could be at any location behind the leading body end 20. Within the aforementioned dimensional ranges, the base portion 44 of the overall U-shaped surface 43, is spaced a distance X, approximately 0.08 inches, from the trailing end 22 but could be values larger or smaller than this distance.

The U-shaped surface 43 is made up of the aforementioned base portion 44 and spaced leg portions 46, 48 projecting away from the base portion 44, each up to a free end 50, 52, respectively.

The notch 24 has an entry location at 54 defined between the free ends 50, 52. In one form, the entry location 54 has an exemplary width dimension X2 in the range of 0.013-0.016 inches.

It should be emphasized that the provided dimensions are exemplary of but one form of the invention. The elongate body 18 may be made like a conventional K-wire or surgical grade pin. It can be made in any length, shape, and diameter, though the lower limit on diameter is dictated by the size and nature of the flexible component/suture 12.

The leg portion 48 of the surface 43 is defined by a cantilevered part 56 on the elongate body 18. The cantilevered part 56 tapers in a leading direction and is rounded about its perimeter at 58, including at its free end 60, which defines the free end 52 of the leg portion 48 of the surface 43.

Contiguous with the leg portion 46 of the surface 43 is a guide surface 62 that is substantially straight and angled with respect to the axis 30. As depicted, the guide surface 62 and leg portion 46 of the surface 43 reside in the same plane, though this is not required. This plane is substantially parallel to a plane containing the leg portion 48 of the surface 43, thereby producing a substantially uniform width dimension X2 for the notch 24 between the entry location 54 and the base portion 44. A uniform width is not required, however. These planes are shown at an angle θ of approximately 10° with respect to the axis 30. Preferably, the range of θ is 5°-15°, with it contemplated that angles outside of this range could be utilized.

The guide surface 62 extends from the peripheral surface 25 of the elongate body 18 whereby the elongate flexible component 12, shown as an exemplary suture, can be slid along the peripheral surface 25 rearwardly up to the location at 64 where the guide surface 62 meets the peripheral surface 25, whereupon the suture 12 can be slid further guidingly angularly inwardly along either of the surface leg portions 46, 48 up to and against the base 44 whereupon the suture 12 assumes the operative position shown in FIG. 3. The drawing surface 26 in this embodiment is defined at the base surface portion 44.

As described, the guide surface 62 is contiguous with the surface 43 and can be viewed as bounding the notch 24. The guide surface 62 may be considered as either bounding, or leading into, the notch 24, but will, for purposes of simplicity, be treated herein as separate therefrom.

The depicted configuration effectively acts as a hook to engage the suture 12. A surgeon has the option of: a) bearing the peripheral surface 25 of the elongate body 18 forwardly of the guide edge 62 against the midlength part 28 of the suture 12 and sliding the elongate body 18 in a forward direction relative to the midlength part 28 to cause the midlength part 28 to slide up to and past the guide edge 62 and into the notch 24 up to the operative position; or b) maintaining the elongate body 18 substantially stationary while manipulating the suture 12 by dragging the midlength portion 28 against the peripheral surface 25 rearwardly up to the guide edge 62 and therealong into the notch 24 and eventually against the drawing surface 26 at the base surface portion 44 to assume the operative position. Regardless of which technique is selected, the operative position for the suture can be quickly and consistently established.

Of course, the surgeon can place the midlength part 28 directly into the notch 24 and the operative position or initially place the midlength part 28 against the elongate body 18 closer to the notch 24 than described above. As a still further option, the midlength part 28 of the suture 12 might be slid along the cantilevered part 56 forwardly and past the free end 52, whereupon the midlength portion 28 separates from the cantilevered part 56 and moves radially inwardly to align with the notch 24, whereupon the midlength part 28 can be readily seated at the drawing edge 26.

In this embodiment, the guide edge 62 has an axial extent greater than an axial extent of the notch 24 whereby there is not a required abrupt transition from the outside surface 32 to the notch 24 which potentially accounts for a more consistent engagement.

As depicted in this form, the cantilevered part 56 does not increase the diameter D1 at all, or appreciably, and thus it does not have a tendency to interfere with movement of the adjacent axial region of the elongate body 18 through the bone passage 16. In other forms the diameter at the cantilevered part may be different from the diameters D1 and/or D. The rounded perimeter 58 and free end 60 further minimize the likelihood of hangup.

The region at 66 at the base of the notch 24 may be contoured, or cut away to provide a receptacle for that portion of the suture 12 projecting rearwardly from the midlength part 28 bearing against the drawing surface 26. A similar configuration may be provided diametrically oppositely on the elongate body 18. This reduces the projection of the suture 12 beyond the diameter D1 and avoids significant binding between the apparatus 10 with the operatively positioned suture 12 and the inside surface of the bone surrounding the passage 16.

All surfaces/edges in the vicinity of the notch 24, and that may contact the suture 12 as it is being moved into the notch 24 and as it assumes the operative position, are preferably without sharp contours as might potentially compromise the integrity of the suture 12 as it is placed in the operative position and drawn through the passage 16.

One exemplary procedure will now be described sequentially and schematically in FIGS. 5-7.

In FIG. 5, the tip 34 is directed against an entry surface 68 on the bone 14. The suture 12 can be directed into the operative position within the notch 24 at this point or after the leading end of the elongate body 18 is directed partially or fully through the bone 14. The suture 12 and apparatus 10 are relatively repositioned to guide the suture 12 into its operative position within the receptacle, as shown in FIG. 3.

As shown in FIG. 6, the apparatus 10 is pressed in a forward/first direction against the bone 14 and turned to cause the cutting edges 38, as seen clearly in FIGS. 3 and 4, to progressively produce the passage/opening 16 or enlarge an existing passage, or part thereof. The turning can be an oscillating movement, back and forth, or a continuous rotation in one direction, either manually or using a drive.

The ability to readily place the suture 12 in the operative position on the same structure that creates or enlarges the passage 16 may simplify surgical procedures by reason of potentially reducing components and/or steps used/practiced during a procedure. For example, in a preferred form, the passage 16 may be formed or enlarged with the apparatus 10 alone, avoiding the need to keep on hand and use a dedicated drilling structure such as a conventional bit or pin. Without having to separate the apparatus 10 from the treated tissue, as required with a conventional drill, the suture 12 can be placed in the operative position and advanced through the passage 16. Thus, the surgeon is afforded the convenience of using a single device to form/enlarge the passage 16 and advance the suture 12 without contending with any tangling of the suture, since the apparatus 10 with the operatively positioned suture need not be turned, other than by potentially slightly shifting it back and forth around its axis to avoid binding within the passage 16.

Further, the ability to form/enlarge the passage 16 and advance the suture 12 without backing the drilling structure out of the passage 16 avoids the surgeon's having to relocate the pre-formed passage 16 to introduce therein the suture itself or the structure that advances the suture into and through the passage 16. That is, at all times, the apparatus 10 and/or the suture 12 may occupy the passage 16, obviating the need for unguided introduction of the suture 12 or advancing apparatus into the formed passage 16.

Of course, the invention contemplates that the apparatus 10 can be used to advance a suture 12 through a pre-formed passage 16 defined by a conventional drilling device.

As shown in FIG. 7, the apparatus 10 can be advanced fully through the passage 16 through an exit opening 70 in the bone 14. With the suture 12 in the operative position, as shown most clearly in FIG. 3, the suture 12 is drawn in a "U" shape with legs L1, L2 projecting rearwardly from a part of the midlength part 28 that bears against the drawing surface 26. The legs L1, L2 fold against the undercut peripheral surface region 66, as seen in dotted lines in FIG. 3, and can be squeezed through the passage 16 without significant interference, particularly given the widened diameter created by the locally radially enlarged leading portion of the elongate body 18.

Once the apparatus 10 is directed fully through the bone 14, as seen in FIG. 7, the suture and apparatus 10 can be readily separated by sliding the midlength part 28 out of the notch 24.

As shown schematically in FIG. 8, the elongate body 18 may have at least one movable part 72 that, upon being repositioned, changes the configuration of the elongate body 18 to avoid inadvertent escape of the suture 12 from its operative position. The movable part 72 may take a number of different forms. One or more part 72 may be guidingly repositionable to change the configuration of the elongate body 18.

As shown in FIG. 9, the function of the schematically represented movable part 72 may be performed by the cantilevered part 56, which is integrally formed with the rest of the elongate body 18. The cantilevered part 56 may be bent from the solid line position into the dotted line position wherein the free end 60 becomes close to or even abuts against the leg portion 46 of the surface 43 to create a fully surrounded receptacle configuration. This reconfiguration effectively blocks the entry location 54. A lesser degree of deformation may change the shape and/or reduce the effective size of the entry location 54 to reduce the likelihood that the midlength portion 28 might escape from the notch 24.

Alternatively, the cantilevered part 56 may be reconfigured, as by deformation, to capture the suture 12 fixedly against the leg portion 46 of the surface 43, as shown in FIG. 10.

In a further variation as shown in FIG. 11, a modified form of the elongate body 18' has a discrete sub-receptacle 74 contiguous with the notch 24'. With this configuration, the elongate body 18' is locally crimped, as indicated by the arrows 76, to cause the cantilevered part 56' to assume the dotted line position wherein passage of the midlength part 28 through notch 24' is substantially blocked. The sub-receptacle 74 remains open to allow the suture 12 to be drawn lengthwise through the sub-receptacle 74 to allow separation of the suture 12 from the elongate body 18'.

In another variation, as shown in FIG. 12, the notch 24" on the elongate body 18" is closer to the leading end 20" than the trailing end 22". The suture 12 moves into, and is engaged within, the notch 24" in the same manner as it moves into, and is engaged within, the notches 24, 24', with the exception that the notch 24" opens oppositely. Accordingly, the apparatus 10" is used by initially being directed leading end first, in a second direction, opposite to the first direction, as described for the apparatus 10, through the bone 14, shown in FIG. 12, whereupon the introduced suture 12 in the operative position is drawn in the first direction, indicated by the arrow 78, oppositely to the direction in which the apparatus 10" is moved in forming or enlarging the bone passage 16. The apparatus 10" is separated from the bone 14 by being withdrawn by further moving in the direction of the arrow 78.

In FIG. 13, a further modified form of apparatus is shown at 10''', which has the same general form as the instrument 10, but incorporates a drill bit configuration 90 at the leading end 20''' thereof. Spiral flutes form cutting edges 38'. The elongate body 18' can be manually turned or turned through a drive 94.

The foregoing disclosure of specific embodiments is intended to be illustrative of the broad concepts comprehended by the invention.

The invention claimed is:

1. A method of directing an elongate flexible component with a length through a part of a human body, the method comprising the steps of:
    obtaining an apparatus comprising an elongate body with a length between a leading end and a trailing end,
    the elongate body having a lengthwise axis, a cutting edge at the leading end, and a peripheral surface extending around the axis,
    the body further having a notch through the peripheral surface and a drawing surface, the notch bounded by a surface portion that extends at an acute angle to the axis of the elongate body whereby the notch opens in one of a leading and a trailing direction;
    directing a midlength part of the elongate flexible component into the notch and causing the elongate flexible component to be guided by the surface portion in a lengthwise direction oppositely to the one of the leading and trailing direction towards the drawing surface to thereby place the elongate flexible component in an operative position on the apparatus; and
    with the elongate flexible component in the operative position, advancing the elongate body through the part of the human body in a first direction and thereby causing: a) a portion of the elongate flexible component to be drawn by the drawing surface through the part of the human body; and b) a drawn length of the elongate flexible component to assume a "U" shape.

2. The method of directing an elongate flexible component through a part of a human body according to claim 1 wherein the step of advancing the elongate body comprises advancing the elongate body so that the notch moves fully through the part of the human body.

3. The method of directing an elongate flexible component through a part of a human body according to claim 1 wherein the step of advancing the elongate body comprises advancing the elongate body fully through part of the human body.

4. The method of directing an elongate flexible component through a part of a human body according to claim 3 further comprising the step of separating the elongate flexible component from the elongate body after the elongate body is advanced fully through the body part.

5. The method of directing an elongate flexible component through a part of a human body according to claim 1 further comprising the step of using the cutting edge to create or enlarge a passage within the part of the human body through which the elongate flexible component is directed.

6. The method of directing an elongate flexible component through a part of a human body according to claim 5 wherein the step of creating or enlarging a passage comprises turning the leading end of the elongate body around the lengthwise axis of the elongate body to cause the cutting edge to sever the part of the human body before directing the midlength part of the elongate flexible component into the notch.

7. The method of directing an elongate flexible component through a part of a human body according to claim 6 wherein the part of the human body is a bone/bone part.

8. The method of directing an elongate flexible component through a part of a human body according to claim 5 wherein the elongate body has a stepped diameter with a larger diameter peripheral surface portion and a smaller diameter peripheral surface portion, the larger diameter peripheral surface portion closer to the leading end of the elongate body than the smaller diameter peripheral surface portion, wherein the step of using the cutting edge comprises creating a passage with the larger diameter peripheral surface portion through which the smaller diameter peripheral surface portion of the elongate body is passed.

9. The method of directing an elongate flexible component through a part of a human body according to claim 1 wherein the step of directing the midlength part of the elongate flexible component into the notch comprises sliding the midlength part of the elongate flexible component against and axially along the peripheral surface of the elongate body up to and into the notch.

10. The method of directing an elongate flexible component through a part of a human body according to claim 1 wherein the step of directing the midlength part of the elongate flexible component into the notch comprises slidably guiding the midlength part of the elongate flexible component inwardly from the outside surface along the surface portion that extends at the acute angle to the lengthwise axis, wherein the acute angle is in a range of 5°-15°.

11. The method of directing an elongate flexible component through a part of a human body according to claim 1 wherein the step of directing the midlength part of the elongate flexible component into the notch comprises guiding the midlength part of the elongate flexible component lengthwise along the elongate body to the surface portion at the acute angle along the surface portion at the acute angle up to and against the drawing surface.

12. The method of directing an elongate flexible component through a part of a human body according to claim 1 further comprising the step of directing the elongate body, leading end first, in a second direction opposite to the first direction, through the part of the human body to expose the notch before directing the midlength part of the elongate flexible component into the notch, and the step of advancing the elongate body comprises moving the elongate body with the elongate flexible component in the operative position, trailing end first, in the first direction to thereby separate the apparatus from the part of the human body.

13. The method of directing an elongate flexible component through a part of a human body according to claim 1 further comprising the step of reconfiguring the apparatus to assist maintaining the elongate flexible component in the operative position.

14. The method of directing an elongate flexible component through a part of a human body according to claim 13 wherein the step of reconfiguring the apparatus comprises deforming a part of the apparatus.

15. The method of directing an elongate flexible component through a part of a human body according to claim 14 wherein the part of the apparatus that is deformed is a cantilevered part bounding a part of the notch and the cantilevered part is integrally formed with the elongate body and bent to perform the step of reconfiguring the apparatus.

16. The method of directing an elongate flexible component through a part of a human body according to claim 13 wherein the notch has an entry location through which the midlength part of the elongate flexible component is directed to place the elongate flexible component in the operative position and the step of reconfiguring the apparatus comprises reconfiguring the apparatus to change at least one of a shape and size of the entry location.

17. The method of directing an elongate flexible component through a part of a human body according to claim 16 wherein the elongate body comprises at least one deformable part and the step of reconfiguring the apparatus comprises deforming the at least one deformable part to thereby cause a part of the elongate flexible element to be fixedly captured on the elongate body.

18. The method of directing an elongate flexible component through a part of a human body according to claim 13 wherein the step of reconfiguring the apparatus comprises crimping a region of the apparatus.

19. The method of directing an elongate flexible component through a part of a human body according to claim 1 wherein the notch has a volume bounded by the drawing surface and the drawing surface is exposed within the notch volume.

20. The method of directing an elongate flexible component through a part of a human body according to claim 1 wherein the elongate flexible component is placed in the operative position after the leading end of the elongate body is directed into the part of the human body.

21. The method of directing an elongate flexible component through a part of a human body according to claim 1 wherein the elongate flexible component is a suture.

22. The method of directing an elongate flexible component through a part of a human body according to claim 1 wherein the step of advancing the elongate body through the part of the human body in the first direction comprises advancing the elongate body leading end first.

23. The method of directing an elongate flexible component through a part of a human body according to claim 1 further comprising the step of pre-forming an opening through the part of the human body before introducing the elongate body into the opening through the part of the human body.

24. The method of directing an elongate flexible component through a part of a human body according to claim 1 wherein the portion of the notch opens in a leading direction.

25. The method of directing an elongate flexible component through a part of a human body according to claim 1 wherein the portion of the notch opens in a trailing direction.

26. The method of directing an elongate flexible component through a part of a human body according to claim 1 wherein the notch is closer to the leading end of the elongate body than the trailing end of the elongate body.

27. The method of directing an elongate flexible component through a part of a human body according to claim 1 wherein the notch is closer to the trailing end of the elongate body than the leading end of the elongate body.

28. The method of directing an elongate flexible component through a part of a human body according to claim 1 wherein the elongate body is substantially straight.

29. A method of directing an elongate flexible component with a length through a part of a human body, the method comprising the steps of:
  obtaining an apparatus comprising an elongate body with a length between a leading end and a trailing end,
  the elongate body having a lengthwise axis and a peripheral surface extending around the axis,
  the body further having a notch through the peripheral surface and a drawing surface;
  directing a midlength part of the elongate flexible component into the notch to thereby place the elongate flexible component in an operative position on the apparatus; and
  with the elongate flexible component in the operative position, advancing the elongate body through the part of the human body in a first direction and thereby causing a portion of the elongate flexible component to be drawn by the drawing surface through the part of the human body; and
  directing the elongate body, leading end first, in a second direction opposite to the first direction, through the part of the human body to expose the notch before directing the midlength part of the elongate flexible component into the notch,
  wherein the step of advancing the elongate body comprises moving the elongate body with the elongate flexible component in the operative position, trailing end first, in the first direction to thereby separate the apparatus from the part of the human body.

30. A method of directing an elongate flexible component with a length through a part of a human body, the method comprising the steps of:
  obtaining an apparatus comprising an elongate body with a length between a leading end and a trailing end,
  the elongate body having a lengthwise axis and a peripheral surface extending around the axis,
  the body further having a notch through the peripheral surface and a drawing surface;
  directing a midlength part of the elongate flexible component into the notch to thereby place the elongate flexible component in an operative position on the apparatus; and
  with the elongate flexible component in the operative position, advancing the elongate body through the part of the human body in a first direction and thereby causing a portion of the elongate flexible component to be drawn by the drawing surface through the part of the human body; and directing the elongate body, leading end first, in a second direction opposite to the first direction, through the part of the human body to expose the notch before directing the midlength part of the elongate flexible component into the notch, wherein the step of advancing the elongate body comprises moving the elongate body with the elongate flexible component in the operative position, trailing end first, in the first direction to thereby separate the apparatus from the part of the human body, wherein the elongate body is substantially straight.

* * * * *